United States Patent [19]

Zimmerman et al.

[11] Patent Number: 5,646,235

[45] Date of Patent: Jul. 8, 1997

[54] REDUCTIVE ALKYLATION OF POLYAMINES

[75] Inventors: Robert LeRoy Zimmerman, Austin; Wheeler Conrad Crawford, Houston; Rodney Frederick Lloyd, Katy, all of Tex.

[73] Assignee: Huntsman Petrochemical Corporation, Austin, Tex.

[21] Appl. No.: 665,989

[22] Filed: Jun. 18, 1996

Related U.S. Application Data

[63] Continuation of Ser. No. 410,847, Mar. 27, 1995, abandoned.

[51] Int. Cl.$^6$ .................................................... C08G 12/04
[52] U.S. Cl. ..................... 528/266; 528/234; 528/266; 564/471; 564/472; 564/473; 564/480
[58] Field of Search ..................... 528/234, 266; 564/471, 472, 473, 480

[56] References Cited

U.S. PATENT DOCUMENTS 5,091,585  2/1992  Su et al. .................................. 564/473

FOREIGN PATENT DOCUMENTS 62-010047  1/1987  Japan.
62-39809   8/1994  Japan.
887563    12/1981  U.S.S.R..

*Primary Examiner*—Samuel A. Acquah
*Attorney, Agent, or Firm*—Russell R. Stolle; Ron D. Brown

[57] ABSTRACT

A method is provided for the preparation of tertiary polyamines by alkylating a polyamine having at least two primary amino groups without the use of excess solvent. More particularly, a tertiary amine is produced by reductively alkylating a polyamine with a carbonyl compound, such as formaldehyde, in a reaction zone while in the presence of a hydrogenation catalyst and hydrogen under reductive conditions. The carbonyl compound is continuously supplied to the reaction zone.

8 Claims, No Drawings

REDUCTIVE ALKYLATION OF POLYAMINES

This is a continuation of a application Ser. No. 08/410,847, filed on Mar. 27, 1995 now abandoned.

FIELD OF THE INVENTION

This invention relates to a method for preparing tertiary amines by the reductive alkylation of polyamines. More specifically, the present invention relates to such a method in which excess solvent is not required to avoid gelation or solid precipitation during the reductive alkylation of polyamines which have at least two primary amino groups. The present invention also relates to such a method which used a Ni—Cu—Cr catalyst.

BACKGROUND OF THE INVENTION

Aliphatic tertiary amines are useful as corrosion inhibitors, urethane catalysts and oil additives. They are also useful as intermediates for the production of quaternary ammonium salts and amphoteric surface active agents such as disinfectants, fungicides, sanitary agents, retarders in dyeing, and antistatic agents. As the use of aliphatic tertiary amines is continuing to expand, the requirements for their quality as intermediates are becoming increasingly stringent. Among other things, tertiary amines are required to be color stable and odorless. Accordingly, impurities that may impart undesired colors or smells to the final product must be kept at low levels.

Various prior art methods for the reductive alkylation of polyamines to prepare tertiary amines are well known. However, in the prior art methods, excess solvent has to be used in order to prevent the reaction mixture of amine-formaldehyde and solvent from gelling or forming a solid. This is particularly true when reductively alkylating a polyamine having at least two primary amino groups. The solvent then has to be removed from the final product. Finally, this solvent has to be disposed of properly, which can be costly. Further, due to the presence of large amounts of solvent, the yields on a per batch basis are decreased because more of the crude reaction effluent is solvent rather than product.

EP 0142868 discloses a process for producing a tertiary amine by alkylating a specific amine, including certain polyamines, with a carbonyl compound, e.g., formaldehyde, in the presence of a hydrogenation catalyst while continuously supplying the carbonyl compound to the reaction zone. However, the specific amine thereof is not a polyamine having at least two primary amino groups. Further, the hydrogenation catalyst must have at least one of Co, Ni, Ru, Rh, Pd or Pt supported on pulverized or granular carbon. Other supports or catalysts were not suitable for providing a color stable and odorless product.

Accordingly, there is a need for a method of reductive alkylation of polyamines having at least two primary amino groups which does not require excess solvent and produces a color stable and odorless product. Further, there is a need for a method of reductive alkylation of polyamines using catalysts which are not supported on carbon.

SUMMARY OF THE INVENTION

In response to this need, an improved method for the reductive alkylation of polyamines having at least two primary amine groups is provided. The method involves the continual addition of a concentrated solution of a carbonyl compound, e.g., formaldehyde, to the reaction mixture at reductive conditions to avoid solid or gel formation. This method provides a high purity, color stable, odorless product and minimizes the amount of waste solvent.

More particularly, there is provided a method for producing a tertiary amine, wherein the method comprises reductively alkylating a polyamine with a carbonyl compound in a reaction zone while in the presence of a hydrogenation catalyst and hydrogen under reductive conditions and continuously supplying the carbonyl compound to the reaction zone. In this sense, "continuously" also would include periodically. The carbonyl compound is a carbonyl compound of formula (I)

wherein $R^1$ and $R^2$ each independently represents a hydrogen atom, a saturated or unsaturated, linear, branched or cyclic aliphatic hydrocarbon group having from 1 to 24 total carbon atoms, an aromatic group-substituted aliphatic hydrocarbon group having at most 24 total carbon atoms, or a substituted or unsubstituted aromatic hydrocarbon group having at most 24 total carbon atoms, or R and $R^2$ in combination form an aliphatic hydrocarbon ring. Preferably, the carbonyl compound is formaldehyde.

Preferably, the reductive conditions comprise a temperature ranging from about 100° C. to about 200° C. and a hydrogen pressure of at least about 25 psig. Optionally, the hydrogen pressure is maintained during the reductively alkylating step by providing additional hydrogen to the reaction zone. When the carbonyl compound contains aromatic groups, these aromatic groups may be reduced during severe reductive conditions, e.g., at the upper portion of the temperature range.

The polyamine is any polyamine having at least two primary amino groups, i.e., groups which have $NH_2$. Examples of such polyamines include polyamines of formula (II)

wherein p is 0 or an integer of 1 to 6, $R^3$ is $(CH_2)_m$—X—$(CH_2)_n$, $CR^4R^5$ or combination thereof, wherein m and n are each independently 0 or an integer of 1 to 6 with the proviso that m+n is an integer of at least 1, X is O or NH (i.e., an imino group), Y, $R^4$ and $R^5$ are each independently a hydrogen atom, a linear or branched alkyl or alkenyl group having at most 24 carbon atoms, a primary amino group, a secondary amino group, or a linear or branched alkyl or alkenyl group having at least one primary or secondary amino group and having at most 24 total carbon atoms, with the proviso that Y is required to be a primary amino group or has a primary amino group only when neither $R^4$ and $R^5$ is present as a primary amino group nor has a primary amino group.

Any hydrogenation catalyst may be used in the method of the present invention. If the hydrogenation catalyst is a Ni—Cu—Cr catalyst, the proviso regarding Y above is dropped.

DESCRIPTION OF THE INVENTION

The process in the present invention involves the reductive alkylation of polyamines having at least two primary amino groups. The polyamines are reacted in a hot reductive atmosphere under reductive conditions in the presence of a hydrogenation catalyst. For example, the reductive atmosphere may be hydrogen. The reductive atmosphere may also contain inert gases. The reactor is pressurized with hydrogen to a pressure of at least 25 psig, preferably from about 50 psig to about 5,000 psig and more preferably from about 100 psig to about 1,500 psig. If the hydrogen is mixed with other gases, i.e., inert gases, the foregoing pressures represent the partial pressure of hydrogen. The reactor contents are heated to a temperature ranging from about 50° C. to about 220° C., preferably from about 100° C. to about 200° C., and more preferably from about 120° C. to about 150° C. During the course of the reaction, a carbonyl compound is continually, including periodically, added to the reaction mixture. The present process produces greater yields of product without the use of additional solvents and without gel or solid formation.

Illustrative carbonyl compounds of formula (I) include saturated or unsaturated, linear, branched or cyclic aliphatic aldehydes such as formaldehyde, acetaldehyde, propanal, hexanal, 2-ethylhexanal, 2-hexenal, 2-nonenal and cyclohexylaldehyde; aromatic group-substituted aliphatic aldehydes such as phenylacetaldehyde and 3-phenylpropanal; aromatic aldehydes such as benzaldehyde, o-, m- or p-tolualdehyde, p-methoxybenzaldehyde, p-chlorobenzaldehyde and 1-naphthylaldehyde; aliphatic ketones such as acetone, 3-pentanone and 2-decanone; alicyclic ketones such as cyclopropanone and cyclohexanone; and aromatic ketones such as acetophenone and benzophenone. These carbonyl compounds may be used either independently or in combination. The carbonyl compounds may be used as an aqueous solution or a non-reactive solvent solution [examples of the solvent include an alcohol (e.g., methanol, ethanol), an ether (e.g., tetrahydrofuran) and a hydrocarbon (e.g., hexane, cyclohexane)], if desired. Examples are methylformcel and formalin. Methylformcel solution is provided as a 55% formaldehyde/45% methanol solution by Hoechst Celanese. Formalin is an aqueous 37 to 50% solution of formaldehyde which may contain 15% methyl alcohol.

The carbonyl compound is used in an amount of from 1 to 1.5 moles, and preferably 1 to 1.05 moles, per mole of active hydrogen on the amino or imino group of the polyamine. If the amount of the carbonyl compound used is less than 1 mole per mole of the active hydrogen defined above, the polyamine, or portions thereof, remains unreacted in the final product. If the amount of the carbonyl group is more than 1.5 moles per mole of the active hydrogen, the cost effectiveness of the process is reduced and an extra and prolonged step is required for removing the residual carbonyl compound.

Illustrative polyamine compounds of formula (I) include: bis(aminoethyl)ether, diethylenetriamine and 1,2-bis (aminoethoxy)ethane. These amines may be used either individually or in combination.

Any hydrogenation catalyst may be used in the present invention. The catalyst may comprise from 0.1 to 10 wt % of Ni, Co, Ru, Rh, Pd or Pt on a support. Alumina, silica, diatomaceous earth and pulverized or granular carbon may be used as supports for the hydrogenation catalyst. Such a hydrogenation catalyst may be prepared by any conventional method, such as the one shown in *Advances in Catalysis*, Vol. 20, p. 112 (1969). Metals and metal oxides such as Raney nickel, Raney cobalt, platinum oxide, platinum black and palladium black are known as hydrogenation catalysts and may be used. Other examples of suitable and commercially available catalysts include Englehard's Ni-1404 (64% nickel on a support), Ni-0104 (58% nickel on a support) and Co-0164 (25% cobalt on a support) catalysts (Englehard Corp., Iselin, N.J.), Mallinckrodt's CALISCAT E-211TR, (50% nickel on a support), E-221TY E-221TU (42% nickel, 4% cobalt and 4% copper on silica) and E-230TR (56% nickel on alumina) catalysts (Mallinckrodt's Specialty Chemicals Co., Erie, Pa.), and United Catalysts' G-96(66% nickel on silica), G-49B (50% on a support) catalysts and G-69B (zirconium-promoted, nickel-on-kieselghur 60% nickel) (United Catalysts Inc., Louisville, Ky.). The hydrogenation catalyst is used in the present invention at the concentration of 5 to 5,000 ppm of the catalyst metal based on the amount of the starting polyamine.

Another suitable catalyst for use in the method of the present invention is one containing nickel, copper and chromium ("Ni—Cu—Cr catalyst"). Such a catalyst is described, for example, in U.S. Pat. No. 3,152,998 and U.S. Pat. No. 3,654,370, which are hereby incorporated by reference. The catalyst disclosed therein is preferably prepared by the reduction of a mixture of the oxides of nickel, copper and chromium in the presence of hydrogen at a temperature ranging from about 250° C. to about 400° C., preferably from about 300° to about 320° C. Preferably, the hydrogen is continuously passed over or through oxide mixture. Calculated on an oxide-free basis, the catalyst contains from about 60 to about 85 mole % nickel, from about 14 to about 37 mole % copper, and from about 1 to about 5 mole % chromium. A particularly preferred catalyst composition disclosed therein is one containing from about 70 to about 80 mole % nickel, from about 20 to about 25 mole % copper, and from about 1 to about 5 mole % chromium. To maintain the physical strength and integrity of pellets of such catalysts, the oxide mixture is preferably reduced so that the amount of metallic nickel therein based on total catalyst weight is at least 30%, preferably at least 35%. Such strength and integrity are factors if the catalyst is used in a fixed bed reactor.

If the Ni—Cu—Cr catalysts are used, the proviso regarding Y in formula (II) is dropped. Illustrative polyamines which would be within formula (II) as so modified would include: 2-aminoethyl cocoalkyl amine, 2-aminoethyl tallowalkyl amine, 3-aminopropyl cocoalkyl amine, 3-aminopropyl tallowalkyl amine, N,N'-dicocoalkyl ethylenediamine, N-cocoalkyl N'-tallowalkyl ethylenediamine, N-cocoalkyl diethylenetriamine, N-tallowalkyl diethylenetriamine, N-cocoalkyl dipropylenetriamine, N-tallowalkyl dipropylenetriamine, N-cocoalkyl tripropylenetetramine, N-tallowalkyl tripropylenetetramine, N-cocoalkyl tetrapropylenepentamine, N-tallowalkyl tetrapropylenepentamine, N-cocoalkyl pentapropylenehexamine, and N-tallowalkyl pentapropylenehexamine. These amines may be used either individually or in combination.

The carbonyl compound may be added by any method that permits its continuous addition, including periodic addition, over the course of the reaction or portion thereof. For example, the carbonyl compound may be supplied in small portions into the reaction zone of a reactor by means of a compressor.

If an aqueous solution of the carbonyl compound is likely to cause a great accumulation of water during the reaction, or if the reaction is expected to produce a large amount of water as a by-product, hydrogen may be released or circulated so as to discharge water out of the system while the reaction is being carried out.

An illustrative method for implementing the present invention is shown below. An autoclave reactor equipped with a stirrer, a compressor and an optional gas circulator with a cooling condenser is charged with the starting polyamine and a hydrogenation catalyst. The temperature in the reactor is elevated to the desired level under stirring, and after the atmosphere of the reactor is replaced by hydrogen, an additional amount of hydrogen is supplied to a predetermined pressure. Subsequently, the carbonyl compound is fed into the autoclave under pressure, and the polyamine is reductively alkylated while optionally maintaining hydrogen pressure at the predetermined pressure. When the removal of the accumulated water from the reaction system is desired to decrease the partial pressure of the water in the reaction system and to accelerate the reaction, a hydrogen gas circulator equipped with a cooling condenser is used to discharge the condensed water out of the system. After all of the carbonyl compound has been fed into the reactor, the reaction is continued for a given period while the temperature and, optionally, hydrogen pressure are held constant.

If polyamine alkylation is performed by the method of the present invention, the intended reaction proceeds in a substantially quantitative manner and the formation of by-products that may impair the quality of the end compound is negligible. Therefore, a crude tertiary amine product that is substantially colorless and odorless is obtained.

The tertiary amine produced by the method of the present invention is highly stable against heat and light. As noted in Example 3, it withstands a daylight exposure test (exposed to daylight at room temperature) for at least 7 months without experiencing any change in color or smell.

This tertiary amine can be used to prepare amine oxides and quaternary ammonium salts. All the products are substantially colorless and odorless and have no problems at all in appearance or quality.

The present invention is further illustrated by the following non-limiting working examples and comparative examples. All parts, percentages or other amounts given throughout this disclosure are by weight unless otherwise indicated.

EXAMPLES

Example 1: Preparation of catalyst

A catalyst was prepared from nickel, copper and chromium oxides according to U.S. Pat. No. 3,152,998. The catalyst had a composition in which the metal content calculated on an oxide-free basis was about 75 mole percent nickel, about 23 mole percent copper and about 2 mole percent chromium. Pellets of ⅛ inch by ⅛ inch were prepared from this composition. The pellets were reduced by heating them in the presence of hydrogen at from about 300° C. to about 320° C.

Example 2: Preparation of Bis(dimethylaminoethyl) Ether

Bis(dimethylaminoethyl) ether was prepared reductively alkylating bis(aminoethyl) ether (CAS. No. 2752-17-2) by the following reaction:

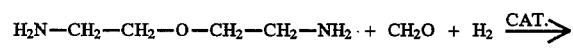

To a 1 liter autoclave reactor was charged 146.6 grams of bis(aminoethyl) ether, and 25 grams of the prereduced, pelleted Ni—Cu—Cr catalyst of Example 1. The reactor was pressurized to about 100 psig with hydrogen and heated to about 120° C. The pressure was then increased to 1,000 psig with hydrogen. Over a 1 ½ hour period, 292 grams of methylformcel solution (55% formaldehyde/45% methanol solution; available from Hoechst Celanese, Bishop, Tex.) was added at a constant rate. Once all the methylformcel solution had been added, no more hydrogen was added so the rate of hydrogen uptake could be monitored and determined. The reaction was held at about 120° C. for about 2 ½ hours and then discharged. After the 2½ hours, no more hydrogen was consumed. The final pressure was about 865 psig. During the reaction, there was no indication of polymer or solid formation. The crude reaction effluent contained about 48% bis(dimethylaminoethyl) ether and about 47% water.

Example 3: Preparation of Pentamethyldiethylenetriamine

To a 1 liter autoclave reactor was charged about 132.3 grams of diethylenetriamine (CAS No. 111-40-0) and 25 grams of the Ni—Cu—Cr catalyst of Example 1. The reactor was pressurized to about 100 psig with hydrogen and then heated to about 120° C. The pressure was then increased to about 1,000 psig with hydrogen. Over a 1½ hour period, 367.8 grams of methylformcel solution was added at a constant rate. The reaction was held at 120° C. for about 3 hours and then discharged. Unlike Example 2, here the hydrogen pressure was maintained at about 1,000 psig for the 3 hours by adding additional hydrogen. There was no indication of polymer or solid formation. The crude reactor effluent contained about 47% pentamethyldiethylenetriamine and about 50% water. The isolated product had a color of 5 Pt-Co (Platinum-Cobalt Color Scale) after seven months exposure to daylight at room temperature. Pt-Co colors also are referred to as APHA colors and Hazen colors.

Example 4: Comparative Example

To a 500 milliliter flask equipped with a mechanical stirrer, thermometer and addition funnel was charged 146.6 grams of bis(aminoethyl) ether. To those was slowly added methylformcel solution. Only about 35 grams of methylformcel could be added before a gel started to form.

In Example 2 which used the same amount of bis (aminoethyl) ether, 292 grams of methylformcel solution was added without gelation occurring. In Example 4, only about 35 grams could be added before a gel formed.

It is understood that the foregoing detailed description and examples are given by way of illustration and that many modifications may be made therein without departing from the spirit or scope of the present invention.

What is claimed is:

1. A method for producing a tertiary amine, said method comprising:

subjecting a polyamine having at least two primary amino groups to a reaction zone in the presence of a hydrogenation catalyst and hydrogen under reductive conditions; and continuously over a predetermined period of time supplying a carbonyl compound to said reaction zone to reductively alkylate said polyamine having at least two primary amino groups, said carbonyl compound is a carbonyl compound of formula (I)

$$R^1-\overset{O}{\underset{\|}{C}}-R^2 \quad (I)$$

wherein $R^1$ and $R^2$ each independently represents a hydrogen atom, a saturated or unsaturated, linear, branched or cyclic aliphatic hydrocarbon group having from 1 to 24 total carbon atoms, an aromatic group-substituted aliphatic hydrocarbon group having at most 24 total carbon atoms, or a substituted or unsubstituted aromatic hydrocarbon group having at most 24 total carbon atoms, or $R^1$ and $R^2$ in combination form an aliphatic hydrocarbon ring.

2. The method of claim 1, wherein the reductive conditions comprise a temperature ranging from about 100° C. to about 200° C. and a hydrogen pressure of at least about 25 psig.

3. The method of claim 2, wherein the hydrogen pressure is maintained during the reductively alkylating step by providing additional hydrogen to the reaction zone.

4. The method of claim 1, wherein said polyamine having at least two primary amino groups is a polyamine of formula (II)

$$H_2N-(R^3)_p-Y,  \quad (II)$$

wherein p is 0 or an integer of 1 to 6, $R^3$ is $(CH_2)_m-X-(CH_2)_n$, $CR^4R^5$ or combination thereof, wherein m and n are each independently 0 or an integer of 1 to 6 with the proviso that m+n is an integer of at least 1, X is O or NH, Y, $R^4$ and $R^5$ each independently represents a hydrogen atom, a linear or branched alkyl or alkenyl group having at most 24 carbon atoms, a primary amino group, a secondary amino group, or a linear or branched alkyl or alkenyl group having at least one primary or secondary amino group and having at most 24 total carbon atoms with the proviso that when said hydrogenation catalyst is other than a Ni—Cu—Cr catalyst, Y is a primary amino group or has a primary amino group when neither $R^4$ and $R^5$ is present as a primary amino group nor has a primary amino group.

5. The method of claim 1, wherein the carbonyl compound is formaldehyde.

6. The method of claim 1, wherein the hydrogenation catalyst is prepared by the reduction of a mixture of oxides of nickel, copper and chromium, the proportion of metals to each other, calculated on an oxide-free basis, being from about 60 to about 85 mole % nickel, from about 14 to about 37 mole % copper and from about 1 to about 5 mole % chromium, and has an amount of metallic nickel therein of at least 30 percent based on the total weight of the hydrogenation catalyst.

7. The method of claim 6, wherein the hydrogenation catalyst is prepared by the reduction of a mixture of oxides of nickel, copper and chromium, the proportion of metals to each other, calculated on an oxide-free basis, being from about 70 to about 80 mole % nickel, from about 20 to about 25 mole % copper and from about 1 to about 5 mole % chromium.

8. A method for producing a tertiary amine, said method comprising:

subjecting a polyamine having at least two primary amino groups to a reaction zone in the presence of a hydrogenation catalyst and hydrogen under reductive conditions; and continuously over a predetermined period of time supplying a carbonyl compound to said reaction zone to reductively alkylate said polyamine having at least two primary amino groups, said carbonyl compound is a carbonyl compound of formula (I)

$$R^1-\overset{\overset{O}{\|}}{C}-R^2 \quad (I)$$

wherein $R^1$ and $R^2$ each independently represents a hydrogen atom, a saturated or unsaturated, linear, branched or cyclic aliphatic hydrocarbon group having from 1 to 24 total carbon atoms, an aromatic group-substituted aliphatic hydrocarbon group having at most 24 total carbon atoms, or a substituted or unsubstituted aromatic hydrocarbon group having at most 24 total carbon atoms, or $R^1$ and $R^2$ in combination form an aliphatic hydrocarbon ring, wherein said polyamine is a polyamine having at least two primary amino groups of formula (II)

$$H_2N-(R^3)_p-Y, \quad (II)$$

wherein p is 0 or an integer of 1 to 6 $R^3$ is $(CH_2)_m-X-(CH_2)_n$, $CR^4R^5$ or combination thereof;

wherein m and n are each independently 0 or an integer of 1 to 6 with the proviso that m+n is an integer of at least 1, X is O or NH, Y, $R^4$ and $R^5$ each independently represents a hydrogen atom, a linear or branched alkyl or alkenyl group having at most 24 carbon atoms, a primary amino group, a secondary amino group, or a linear or branched alkyl or alkenyl group having at least one primary or secondary amino group and having at most 24 total carbon atoms, and wherein the hydrogenation catalyst is prepared by the reduction of a mixture of oxides of nickel, copper and chromium, the proportion of metals to each other, calculated on an oxide-free basis, being from about 60 to about 85 mole % nickel from about 14 to about 37 mole % copper and from about 1 to about 5 mole % chromium, and has an amount of metallic nickel therein of at least 30 percent based on the total weight of the hydrogenation catalyst.

* * * * *